United States Patent
Wang

(10) Patent No.: US 9,498,106 B2
(45) Date of Patent: Nov. 22, 2016

(54) FULL HD TRANSMISSION ORAL CAVITY PHOTOGRAPHIC APPARATUS

(71) Applicant: MONITEX INDUSTRIAL CO., LTD., New Taipei (TW)

(72) Inventor: Shu-Lung Wang, New Taipei (TW)

(73) Assignee: MONITEX INDUSTRIAL CO., LTD., New Taipei (TW)

( * ) Notice: Subject to any disclaimer, the term of this patent is extended or adjusted under 35 U.S.C. 154(b) by 432 days.

(21) Appl. No.: 14/165,060

(22) Filed: Jan. 27, 2014

(65) Prior Publication Data

US 2015/0208910 A1    Jul. 30, 2015

(51) Int. Cl.
 *A61B 1/06*    (2006.01)
 *A61B 1/00*    (2006.01)
 *A61B 1/247*    (2006.01)
 *A61B 1/05*    (2006.01)

(52) U.S. Cl.
 CPC ....... *A61B 1/00124* (2013.01); *A61B 1/00016* (2013.01); *A61B 1/00034* (2013.01); *A61B 1/05* (2013.01); *A61B 1/247* (2013.01); *A61B 1/00022* (2013.01); *A61B 1/00045* (2013.01); *A61B 1/0684* (2013.01); *A61B 2560/0456* (2013.01)

(58) Field of Classification Search
 CPC .. A61B 1/0684; A61B 1/24; A61B 1/00124; A61B 1/00016; A61B 1/00045; A61B 1/00022; A61B 1/247; A61B 1/000347; A61B 1/05; A61B 2560/0456; A61C 7/00
 USPC ............................................... 433/24, 27, 30
 See application file for complete search history.

(56) References Cited

U.S. PATENT DOCUMENTS

| | | | |
|---|---|---|---|
| 2013/0108981 A1* | 5/2013 | Duret ....................... | A61B 1/24 433/30 |
| 2014/0205964 A1* | 7/2014 | Hultgren ................... | A61C 7/00 433/24 |
| 2014/0272764 A1* | 9/2014 | Miller ...................... | A61B 1/0684 433/27 |

\* cited by examiner

*Primary Examiner* — Glenn Richman
(74) *Attorney, Agent, or Firm* — Muncy, Geissler, Olds & Lowe, P.C.

(57) ABSTRACT

A full HD transmission oral cavity photographic apparatus comprises a photographic portion and a grip portion. The photographic portion includes an image sensor to capture a full HD image and a light source. The grip portion includes a control circuit electrically connected to the image sensor and a transmission interface electrically connected to the control circuit. The transmission interface includes a Wi-Fi Peer-to-Peer transmission module which can transmit the full HD image via Wi-Fi Peer-to-Peer transmission to a display device for displaying.

8 Claims, 4 Drawing Sheets

FULL HD TRANSMISSION ORAL CAVITY PHOTOGRAPHIC APPARATUS

FIELD OF THE INVENTION

The present invention relates to an oral cavity photographic apparatus and particularly to an oral cavity photographic apparatus capable of transmitting full HD (High Definition) images.

BACKGROUND OF THE INVENTION

An oral cavity photographic apparatus mainly aims to take images inside a patient's mouth through a photographic lens and transmit the images to a computer display screen on a treatment table to allow the patient to directly see the inside condition of the mouth and facilitate two-way communication between the doctor and the patient. The images also can further be saved in a display device such as a tablet computer or notebook computer so that the doctor can use these images for tutorial purpose or academic exchange.

Furthermore, some conventional oral cavity photographic apparatus can also transmit the images captured by the photographic lens through wired or wireless transmission to a display device for displaying. The image usually is presented in an image quality through a Video Graphic Array (VGA) with a resolution of 640×640 pixels. The image thus formed is a rather lower end type and cannot fully keep the details of the oral image. Moreover, when the VGA quality image is used for tutorial or academic exchange purpose, its lower resolution pixels cannot fully reveal the image details in projection to result in an undesirable total visual effect.

In addition, the conventional wireless transmission oral cavity photographic apparatus generally adopts radio frequency of 2.4 GHz for image transmission and receiving. Its transmission bandwidth limitation can only generate lower VGA image pixels. The images also are prone to be interfered by external environments to result in signal interruption or blurred images. This also makes maintaining quality of image records and photography difficult.

SUMMARY OF THE INVENTION

The primary object of the present invention is to overcome the problems of the conventional wireless transmission oral cavity photographic apparatus that the images captured by the oral cavity photographic apparatus are easily interfered by external environments to result in signal interruption and blurred images.

To achieve the foregoing object, the present invention provides a full HD transmission oral cavity photographic apparatus which includes a photographic portion entered into a patient's oral cavity to get images inside the oral cavity and a grip portion connected to the photographic portion. The photographic portion includes an image sensor to capture a full HD image from the interior of the oral cavity and a light source abutting the image sensor. The grip portion includes a control circuit electrically connected to the image sensor and light source, and a transmission interface electrically connected to the control circuit. The transmission interface includes a Wi-Fi Peer-to-Peer transmission module. The control circuit drives the Wi-Fi Peer-to-Peer transmission module to transmit the full HD image through Wi-Fi Peer-to-Peer transmission to a display device for displaying.

In one aspect the image sensor is a high resolution CMOS image sensor.

In another aspect the high resolution CMOS image sensor includes an optical multi-piece and wide angle macro lens.

In yet another aspect the light source is an LED (Light-emitting diode) lamp or an UV (Ultraviolet ray) lamp.

In yet another aspect the grip portion includes an electric power unit electrically connected to the control circuit to supply electric power to the control circuit.

In yet another aspect the transmission interface includes an output port connected to the control circuit to transmit the full HD image via a transmission cable to the display device.

In yet another aspect the output port is an USB (Universal Serial Bus) connection port or an HDMI (High-Definition Multimedia Interface) connection port.

In yet another aspect the transmission interface includes a memory card slot connected to the control circuit to receive insertion of an SD memory card. The control circuit receives the full HD image from the image sensor and saves the full HD image in the SD memory card.

The invention thus formed can provide many benefits, including: 1. a full HD image can be captured through the image sensor; 2. the full HD image can be steadily transmitted via the Wi-Fi Peer-to-Peer transmission module without being interfered by external environment to overcome the problems of signal interruption or blurred images.

The foregoing, as well as additional objects, features and advantages of the invention will be more readily apparent from the following detailed description, which proceeds with reference to the accompanying drawings.

DETAILED DESCRIPTION OF THE PREFERRED EMBODIMENT

Figure 1:
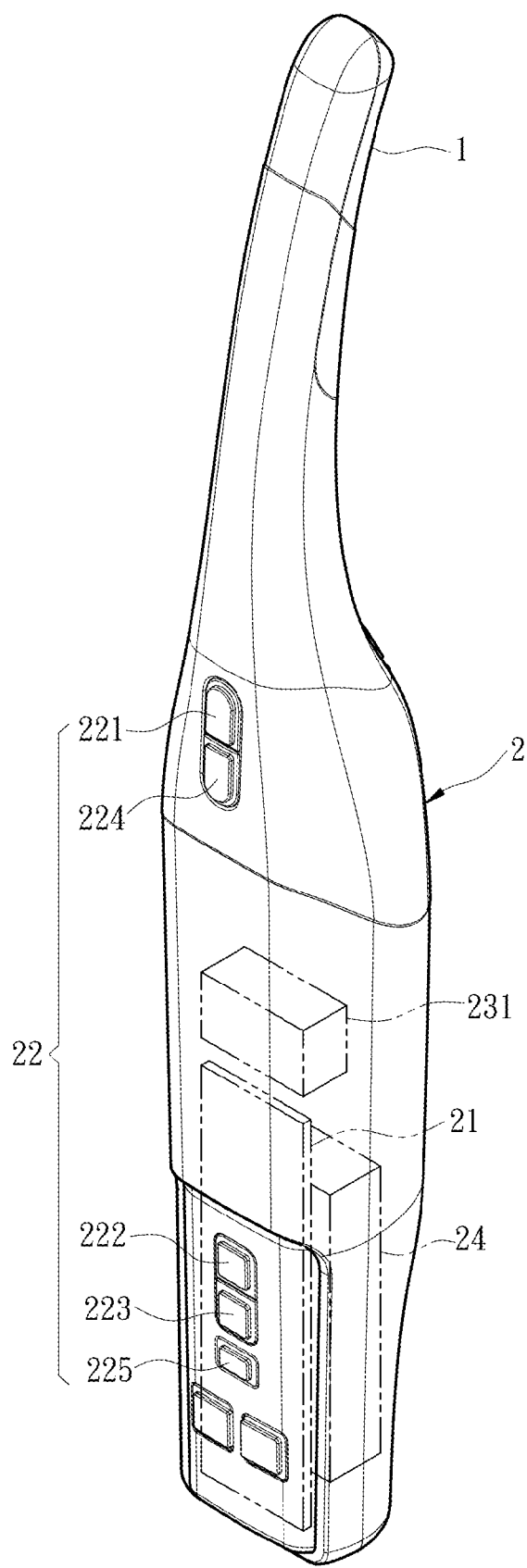
FIG. 1 is a perspective view of an embodiment of the invention.
Figure 2:
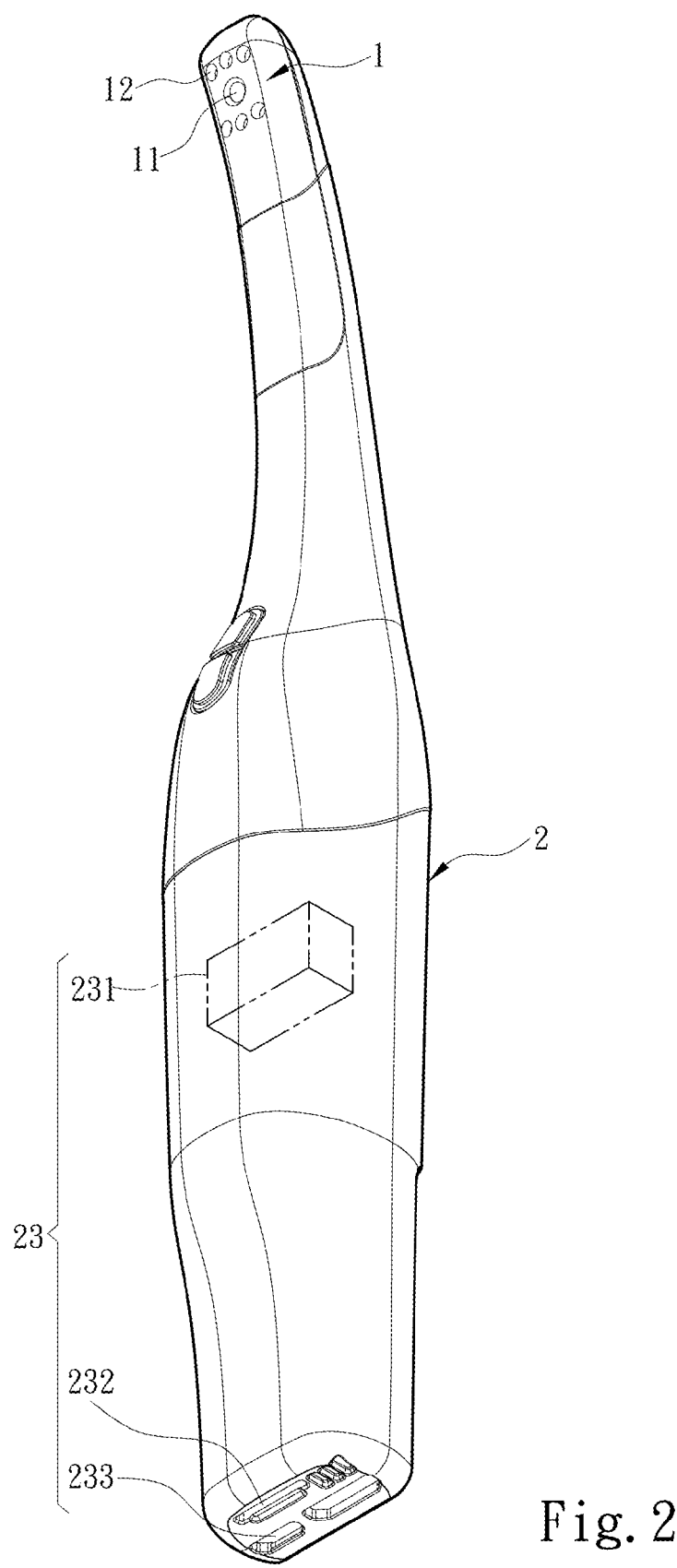
FIG. 2 is another perspective view of an embodiment of the invention.

Please refer to FIGS. 1 and 2 for an embodiment of the full HD transmission oral cavity photographic apparatus of the invention. It comprises a photographic portion 1 entered into a patient's oral cavity to get images inside the oral cavity and a grip portion 2 connected to the photographic portion 1. The photographic portion 1 includes an image sensor 11 to capture a full HD (High Definition) image from the interior of the oral cavity and a light source 12 abutting the image sensor 11 to provide desired illumination. The image sensor 11 can be a high resolution CMOS (Complementary Metal-Oxide-Semiconductor) image sensor including an optical multi-piece and wide angle macro lens. The light source 12 can be an LED (Light-Emitting Diode) lamp or an UV (Ultraviolet Ray) lamp. In this embodiment, the image sensor 11 has two rows of the light sources 12 respectively at the front side and rear side thereof 11 to project light such that the image sensor 11 can clearly capture the inside condition of the patient's oral cavity.

The grip portion 2 includes a control circuit 21 electrically connected to the image sensor 11 and light source 12, a function key set 22 depressible to generate a command signal to the control circuit 21, a transmission interface 23 electrically connected to the control circuit 21, and an electric power unit 24 connected to the control circuit 21 and transmission interface 23 to supply electric power needed. The function key set 22 includes a shooting button 221 to drive the photographic portion 1 to take the image, a zoom in button 222 to control the image sensor 11 to take the image at a shorter distance, a zoom out button 223 to control the image sensor 11 to take the image at a longer distance, a file saving button 224 and a delete button 225. The transmission interface 23 includes a Wi-Fi (Wireless Fidelity) Peer-to-Peer transmission module 231 and a memory card slot 232 connected to the control circuit 21 to receive insertion of an SD (Secure Digital) memory card. The SD memory card can be a Wi-Fi SD memory card (Wi-Fi Secure Digital Memory Card).

Figure 3:
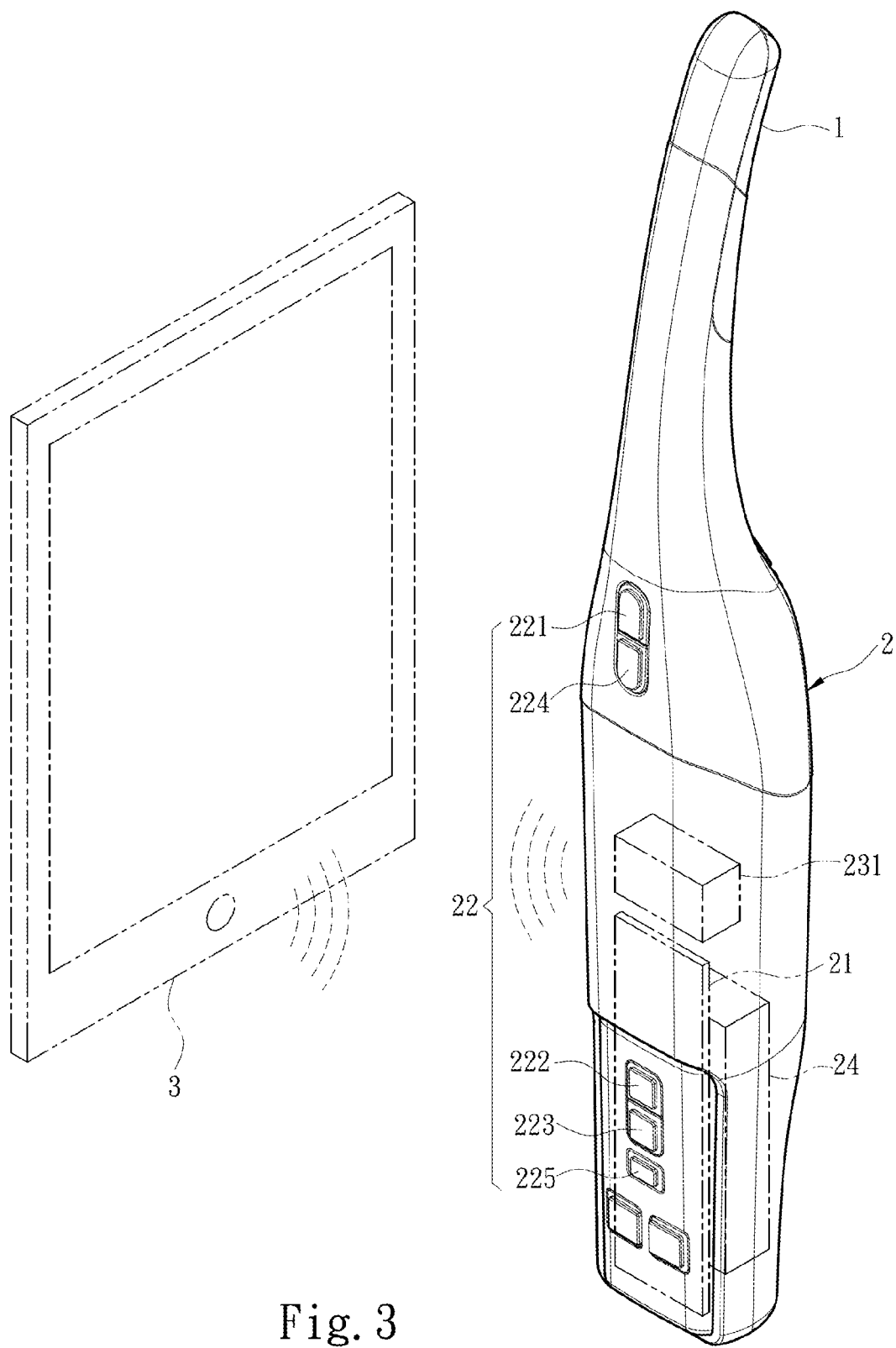
FIG. 3 is a schematic view of an embodiment of the invention in a use condition.

Please refer to FIG. 3, in practice, the full HD transmission oral cavity photographic apparatus of the invention is linked to a display device 3 which can be a tablet computer, handset or the like. The display device 3 is installed with application software corresponding to the full HD transmission oral cavity photographic apparatus. Through the application software, the display device 3 can receive commands of the full HD transmission oral cavity photographic apparatus to perform corresponding operations. After the full HD transmission oral cavity photographic apparatus and display device 3 are connected, and the shooting button 221 is depressed by a user, the control circuit 21 drives the light source 12 to generate light and drives the image sensor 11 to start capturing the full HD image; then the control circuit 21 can get the full HD image from the image sensor 11, and transmit the full HD image to the SD memory card and also transmit synchronously the full HD image through Wi-Fi Peer-to-Peer transmission via the Wi-Fi Peer-to-Peer transmission module 231 to the display device 3 for displaying. During image taking operation, the user can control the full HD image scope captured by the image sensor 11 via the zoom in button 222 and the zoom out button 223. After the image taking operation is finished, the user can push the file saving button 224 to save the full HD image in the SD memory card and display device 3. In the event that the full HD image does not meet user's satisfaction, it can be deleted by pressing the delete button 225.

Aside from the wireless transmission previously discussed, the full HD transmission oral cavity photographic apparatus of the invention also can transmit the full HD image via wired transmission. The transmission interface 23 includes at least one output port 233 connected to the control circuit 21. The output port 233 also is connected to the display device 3 via a transmission cable (not shown in the drawings) to transmit the full HD image to the display device 3. The output port 233 can be an USB (Universal Serial Bus) connection port or an HDMI (High-Definition Multimedia Interface) connection port that provides plug-and-play function.

Figure 4:
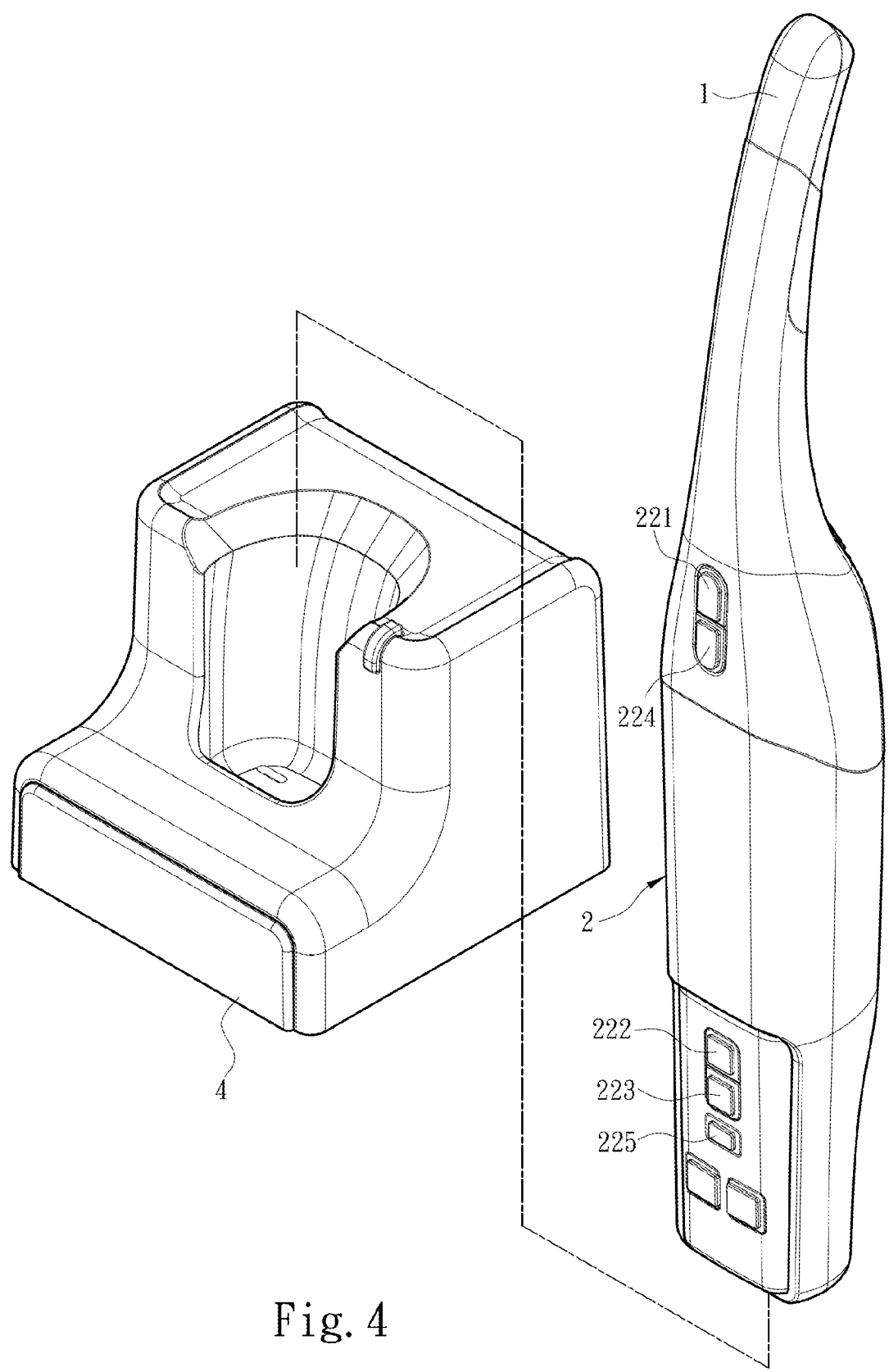
FIG. 4 is a schematic view of an embodiment of the invention in another use condition.

In addition, please refer to FIG. 4, the full HD transmission oral cavity photographic apparatus of the invention can also be collaborated with a charging socket 4 which is coupled with the grip portion 2 to get commercial power to supply to the electric power unit 24. The electric power unit 24 can be a charge battery to store the electric power provided by the charging socket 4 so that the full HD transmission oral cavity photographic apparatus can be used without connecting to a power cord to improve usability.

As a conclusion, the full HD transmission oral cavity photographic apparatus of the invention can capture a full HD image through the image sensor 11, and transmit the full HD image synchronously via the Wi-Fi Peer-to-Peer transmission module 231 to the display device 3 for saving. Alternatively, the full HD image also can be saved in the SD memory card via the memory card slot 232, or transmitted via wired transmission through the output port 233 to the display device 3. Thus, no matter the full HD image is transmitted through wired or wireless transmission, it can be transmitted as desired. Moreover, by transmitting the full HD image through the Wi-Fi Peer-to-Peer transmission module 231, image transmission quality and steadiness can be greatly improved. Thus, the image can be captured and displayed at the 1920×1080 Full HD level, and the frame rate per second can reach 30 fps, hence can effectively overcome the problem of image signal interruption or blurred image in the conventional oral cavity photographic apparatus.

What is claimed is:

1. A full HD transmission oral cavity photographic apparatus, comprising:
   a photographic portion which is entered into a patient's oral cavity to get an inner image of the oral cavity and includes an image sensor to capture a full HD (High Definition) image from an interior of the oral cavity and a light source abutting the image sensor; and
   a grip portion which is connected to the photographic portion and includes a control circuit electrically connected to the image sensor and the light source, a function key set depressible to generate a command signal to the control circuit, and a transmission interface electrically connected to the control circuit and including a Wi-Fi (Wireless Fidelity) Peer-to-Peer transmission module, wherein the function key set includes a shooting button to drive the photographic portion to take the image, a zoom in button to control the image sensor to take the image at a shorter distance, a zoom out button to control the image sensor to take the image at a longer distance, a file saving button and a delete button;
   wherein the control circuit drives the Wi-Fi Peer-to-Peer transmission module to transmit the full HD image via Wi-Fi Peer-to-Peer transmission to a display device for displaying.

2. The full HD transmission oral cavity photographic apparatus of claim 1, wherein the image sensor is a high resolution CMOS (Complementary Metal-Oxide-Semiconductor) image sensor.

3. The full HD transmission oral cavity photographic apparatus of claim 2, wherein the high resolution CMOS image sensor includes an optical multi-piece and wide angle macro lens.

4. The full HD transmission oral cavity photographic apparatus of claim 1, wherein the light source is an LED (light-emitting diode) lamp or an UV (ultraviolet ray) lamp.

5. The full HD transmission oral cavity photographic apparatus of claim 1, wherein the grip portion includes an electric power unit electrically connected to the control circuit to supply electric power to the control circuit.

6. The full HD transmission oral cavity photographic apparatus of claim 1, wherein the transmission interface includes an output port connected to the control circuit to transmit the full HD image to the display device through a transmission cable.

7. The full HD transmission oral cavity photographic apparatus of claim 6, wherein the output port is an USB (Universal Serial Bus) connection port or an HDMI (High-Definition Multimedia Interface) connection port.

8. The full HD transmission oral cavity photographic apparatus of claim 1, wherein the transmission interface includes a memory card slot connected to the control circuit to receive insertion of an SD (Secure Digital) memory card, the control circuit receiving the full HD image from the image sensor and saving the full HD image in the SD memory card.

* * * * *